Nov. 1, 1960 O. O. DUNHAM Plant Pat. 1,980
CHRYSANTHEMUM PLANT
Filed July 27, 1959
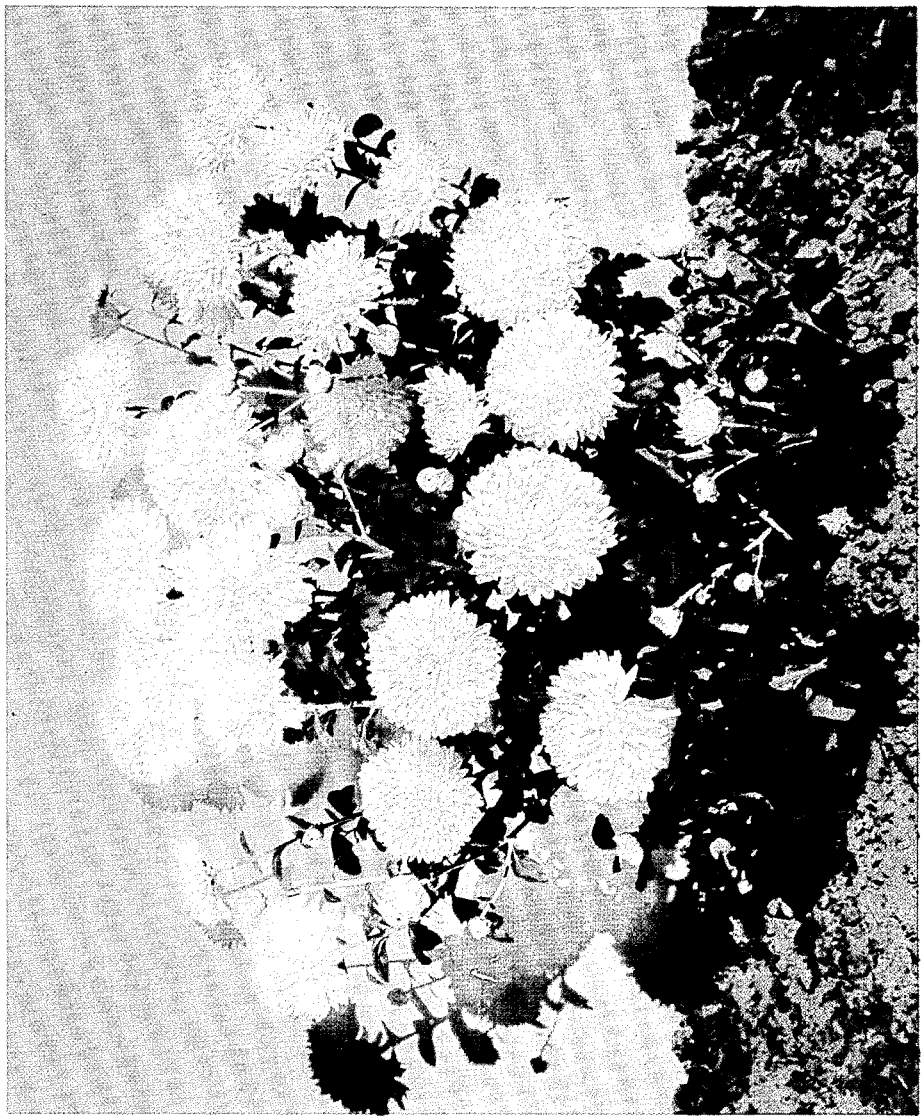
Inventor
O. O. Dunham
by Robb & Robb
Attorneys United States Patent Office Plant Pat. 1,980
Patented Nov. 1, 1960

1,980

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,947

1 Claim. (Cl. 47—60)

My present invention comprises a new and distinct variety of chrysanthemum plant, which is the result of crossing the variety known as "Balcombe Yellow" (unpatented), which is an English garden chrysanthemum and the unpatented variety which I designate as "No. 5350".

The object of my invention has been to produce a new variety of chrysanthemum plant of vivid yellow color and upright growth and habit as well as earliness of bloom.

In the development of the present variety, I have undertaken a program which has been directed to careful selection and crossbreeding of so-called American garden chrysanthemums and English early chrysanthemums, with the view of producing new varieties which have the attributes of both including the upright growth and habit and earliness previously mentioned, with different colors in the various blooms of such plants being likewise a consideration.

As a result of the specific hybridization above mentioned, I have produced the present new and distinct variety of chrysanthemum plant, which is characterized by the upright growth and habit mentioned as well as the earliness, the vivid yellow of the blooms being a further attribute, and the very double arrangement of the petals, the vigorous, dwarf, compact habit of growth and much earlier, longer blooming period of uninterrupted production of blooms during such period being essential results of this program and found to exist in the particular plant herein referred to.

The blooms of my new variety are a vivid yellow color generally (Nickerson Color Fan produced by Munsell Color Company). As grown in the vicinity of Niles, Michigan, under uniform culture, plants of my new variety have somewhat larger than average blooms and appear on very vigorous stems which are branching and compact in over-all aspect.

While the color of my new variety is more nearly the vivid yellow of the "Balcombe Yellow" parent, from which parent the taller aspects of the plant derive, the earliness of the variety is attributed to the seed parent "No. 5350." The flower type derives from the pollen parent "Balcombe Yellow."

In considering the color of the bloom of my new variety, it is noted that the same is of the "Balcome Yellow" type of vivid yellow and as contrasted with the pink color of my variety "No. 5350." The petal arrangement in the plant hereof is very double and the number of petals is practically innumerable under normal conditions.

The blooms are borne in clusters and of somewhat irregular number on long stems which are strong, the blooms retaining their form to the end.

In the region of Niles, Michigan, where the hybridization has taken place and where first year plants of my new variety have been grown in large numbers, the blooms average about four inches in diameter when full.

The foliage of my plant appears about the same as other plants of the same general type and is relatively large in size and abundant in quantity.

My new variety has been found to retain its distinctive characteristics through successive asexual reproduction.

My new avriety has been asexually reproduced in the vicinity of Niles, Michigan by cuttings.

The accompanying drawing, forming a part hereof, shows a typical plant of my new variety of chrysanthemum.

The following is a detailed description of my new variety of chrysanthemum plant, the color references being to the Nickerson Color Fan published by Munsell Color Company:

Parentage: Seedling.
*Seed parent.*—No. 5350 (unpatented).
*Pollen parent.*—"Balcombe Yellow" (unpatented).
Classification: Botanic.—*Chrysanthemum indicum.*

*Flower*

Blooming habit: Blooms profusely from early September until killing frost; blooms are of continuous production. Observations on which the description is based were made of the plants at Niles, Michigan, in September.

Bud:
*Size.*—Large.
*Form.*—Short with flat top. Not affected by hot or wet weather.
*Peduncle.*—Very long.
*Aspect.*—Rough.
*Color.*—Medium green.
*Strength.*—Stiff; erect.
*Opening.*—Bud opens well; somewhat affected by adverse conditions.

Bloom:
*Size.*—Medium. Average size when fully expanded —4 inches (disbudded).
*Borne.*—In clusters.
*Stems.*—Long; strong.
*Form.*—When first opened—flat. Permanence—retains its form to the end.
*Petalage.*—Very double. Number of petals under normal conditions—innumerable.
*Color.*—When petals begin to unfurl—Munsell Hue 5Y 9/12 vivid yellow. When the bloom is half blown: inside of petals—Munsell Hue 5Y 8/12 vivid yellow; reverse of petals—Munsell Hue 7.5Y 9/8 brilliant greenish yellow. Color of full blown bloom — center of flower — 2.5Y 8/12 Munsell Hue 2.5Y. Outer petals— 2.5Y 8/12 Munsell Hue 2.5Y. Base of petals (singlet)—2.5Y 8/12 Munsell Hue 2.5Y. Inside of petals—2.5Y 8/12 Munsell Hue 2.5Y. Reverse of petals—2.5Y 9/9 Munsell Hue 2.5Y. General tonality from a distance—2.5Y 9/9 Munsell Hue 2.5Y.
*Discoloration.*—General tonality at end of: First week—retains same color. Second week—retains much the same color. Third week—retains much the same color.

Petals:
*Texture.*—Thin. Is affected in hot weather by bleaching. Wet weather produces some fungus infection.
*Appearance.*—Inside—velvety. Outside—satiny.
*Form.*—Pointed.
*Arrangement.*—Imbricated.
*Persistance.*—Hang on and dry.
*Lastingness.* — On the plant—very long. As cut flower—long.

Genital Organs:
*Stamens, anthers.*—Small; few.
*Color.*—Yellow.

*Arrangement.*—Regular around styles.
*Stamens, filaments.*—Short.
*Color.*—White.
*Styles.*—Columnar.
*Length.*—Short.
*Stigmas.*—White.
*Ovaries.*—All enclosed in calyx.
Fruit: Variety is fertile with own pollen.
*Form.*—Oblong shaped.
*Aspect.*—Rough.
*Color at maturity.*—Brownish grey.

*Plant*

Form: Bush.
Growth: Vigorous; dwarf; branching; compact.
Foliage:
*Size.*—Large.
*Quantity.*—Abundant.
*Color.*—New foliage: Upper side—normal green; under side—light green. Old foliage: upper side—dark green; under side—dark green.

*Shape.*—Three lobed.
*Texture.*—Smooth upper side; flat. Velvety under side. Ribs and veins—ordinary.
*Edge.*—Smooth.
*Leaf stem.*—Green in color. Under side—smooth.
*Stipules.*—Short.
*Disease resistance.*—Is affected by mildew under certain conditions.

I claim:

A new and distinct variety of chrysanthemum plant substantially as herein disclosed, characterized as to novelty by the vivid yellow of its blooms, the very double arrangement of the petals, the vigorous, dwarf, compact habit of growth, its much earlier, longer blooming period and uninterrupted production of blooms during such period.

No references cited.